United States Patent [19]

von Itter

[11] Patent Number: 5,026,852

[45] Date of Patent: Jun. 25, 1991

[54] PROCESS FOR THE PREPARATION OF CYTOSINES

[75] Inventor: Franz-Albert von Itter, Bonn, Fed. Rep. of Germany

[73] Assignee: Huels Aktiengesellschaft, Marl, Fed. Rep. of Germany

[21] Appl. No.: 460,424

[22] Filed: Jan. 3, 1990

[30] Foreign Application Priority Data

Mar. 3, 1989 [DE] Fed. Rep. of Germany ....... 3906855

[51] Int. Cl.$^5$ ........................................... C07D 239/47
[52] U.S. Cl. ..................................................... 544/317
[58] Field of Search ......................................... 544/317

[56] References Cited

FOREIGN PATENT DOCUMENTS 59-93059 5/1984 Japan .................................. 544/317

*Primary Examiner*—John M. Ford
*Attorney, Agent, or Firm*—Felfe & Lynch

[57] ABSTRACT

Cytosines which may optionally be substituted in the 5 position are prepared by a simplified process in which urea is reacted with an alcoholate and an alkoxy-acrylonitrile or dialkoxy-propionitrile in a sparsely water-miscible organic solvent which is inert under the reaction conditions. The use of such a solvent makes it possible to react the mentioned reactants in simple fashion without isolation of an intermediate stage, and to reuse the organic solvent without a separate purification.

11 Claims, No Drawings

PROCESS FOR THE PREPARATION OF CYTOSINES

FIELD OF THE INVENTION

The invention relates to a process for the preparation of cytosines, which may optionally be substituted in the 5-position, from β-alkoxy-acrylonitriles and/or β,β-dialkoxy-propionitriles and urea in the presence of alcoholates and subsequent neutralization.

BACKGROUND OF THE INVENTION

It is known to react the above-mentioned starting materials in alcohols as solvents. The reaction is preferably performed in secondary or tertiary alcohols, where the alcoholate and the alcohols correspond to each other.

For example, European Patent 0 082 339 describes the preparation of cytosine from unsubstituted nitriles in tert.butanol in the presence of potassium tert. butylate. The yield of no more than 62.3% is unsatisfactory. This yield is achievable only with the secondary and tertiary alcohols, but these are relatively expensive. The lower alkanols, ethanol and methanol, together with their alcoholates, produce even smaller yields.

In accordance with West German Patent 34 34 142, the reaction is performed in two stages. First, an alkali metal salt of urea in suspension or preferably as a solid substance is formed. In this first step lower alkanols may optionally also be used. Of disadvantage is the necessity of removing the alcohol as completely as possible in or after the first step, because otherwise the second step does not go to completion. This requires expensive technical procedures and equipment. In the second process step the reaction with nitriles, also in alcohols, takes place; this reaction produces yields of up to 70% only if the first step is performed as indicated above. The disadvantage is the two-step feature of the process, the double use of alcohols and the limitation of the reaction temperature to 90° C. in the first step, because otherwise the alkali metal salt of urea decomposes and the yield drops drastically. The regeneration of the solvent is cost-and labor-intensive, especially because only anhydrous alcohols can be used over again.

OBJECTS OF THE INVENTION

It is therefore an object of the present invention to improve and simplify the process for the preparation of cytosines as well as to achieve good or improved yields. If possible the recovery of the urea salt in a separate step is to be avoided.

Another object of the present invention is to simplify the purification of the solvent for the purpose of recycling.

Other objects and advantages of the present invention will be become apparent as the description thereof proceeds.

DESCRIPTION OF THE INVENTION

I have discovered that the reaction of the above-mentioned starting materials can be performed with organic solvents or solvent mixtures which are inert under the reaction conditions and are sparsely miscible with water. The utility of these substantially non-polar aprotic solvents is in direct contradiction to the heretofore used polar alcohol solvents.

Thus the subject matter of the present invention is a process for the preparation of cytosines of the formula

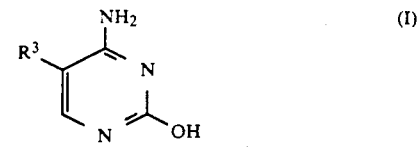

wherein $R^3$ is aralkyl, hydrogen or alkyl of 1 to 6 carbon atoms, by reacting a β-alkoxy-acrylonitrile of the formula

wherein $R^1$ is alkyl of 1 to 6 carbon atoms which may be alkoxy- or halo-substituted and $R^3$ has the meanings defined above, and/or a β,β-dialkoxy-propionitrile of the formula

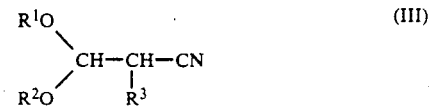

wherein $R^1$ and $R^3$ have the meanings defined above, and $R^2$ is alkyl of 1 to 6 carbon atoms which may be alkoxy- or halo-substituted, with urea in the presence of an alkali metal alcoholate of the formula $MeOR^4$ wherein $R^4$ is alkyl of 1 to 4 carbon atoms and Me is an alkali metal, at temperatures of 0° to 150° C., and separation and recovery of the cytosine by neutralization, wherein a sparsely water-miscible, organic solvent or solvent mixture which is inert under the reaction conditions is used a the reaction medium. The reaction medium may optionally contain alcohols as minor components. A surprising aspect of the present invention is that alcoholates of any desired alcohols, even those of lower alkanols such as ethanol and possibly methanol, can be used.

The separation of the alcohol liberated from these alcoholates in anhydrous form and separate from the solvent which is used is possible in a very simple manner. The solvents which are employed are also recoverable in simple fashion.

Examples of suitable inert, sparsely water-miscible organic solvents are hydrocarbons such as hexane, heptane or the isomeric octanes, cyclohexane, cycloheptane, nitroethane, chlorobenzene, nitrobenzene and/or ethers such as anisole, dibenzylether or diethyleneglycolether. Especially preferred are alkyl aromatics such as xylene, cumene, toluene or ethylbenzene. A common property of such solvents is the aprotic behavior, that is, a minor or complete absence of dissociation accompanied by release of hydrogen ions.

The process according to the present invention makes it possible to react urea and alcoholate with the nitrile reactants II and III in simple fashion, without having to isolate an intermediate alkali metal salt of urea. Whereas, in accordance with European patent 0 082 339, drastic yield losses result when the indicated reactants are reacted in a lower alkanol such as ethanol, the employment of the solvents in accordance with the present invention also make it possible to carry out the reaction in the presence of lower alkanols, provided these are present only as minor components. In the reaction of the urea with the alcoholate, the solvent which is employed should contain less than 30, and preferably less than 20% by weight of alcohol. A further advantage of the process according to the present invention is that the mixture of urea and alcoholate is stable even above the critical temperature of 90° C. of the indicated alcohols.

In accordance with the present invention, the reaction is performed in the temperature range of 0° to 150° C., where the admixture of the reactants is carried out at 0° to 130° C. and the completion of the reaction is effected in the temperature range of 60° to 130° C.

The reaction is preferably carried out by first combining the urea and the alcoholate at temperatures of 0° to 60° C., and subsequently continuously or in portions adding the β-alkoxy-acrylonitrile (II) and/or the β,β-dialkoxy-propionitrile (III) at temperatures of 60° to 130° C.

The addition of the nitrile reactant may take place over a period of 0.5 to 2 hours. The reaction time is 0.5 to 6 hours, depending upon the reaction temperature and the rate of addition of the nitrile reactant.

The alcoholates are preferably alkali metal alcoholates of lower alkanols, preferably the alcoholates of sodium or potassium. The alkoxy radical of the alcoholates have preferably 1 to 4 carbon atoms, and especially preferably 2 carbon atoms. The alcoholate is preferably employed as a suspension in the reaction solution or in the solvent. The molar ratio of urea to alcoholate should be 0.5 to 5:1, preferably 1 to 1.4:1.

The molar ratio of urea to nitrile reactant II and/or III should be 0.5 to 5:1 preferably 1 to 2:1. Taking into consideration the prevailing materials costs, it is of advantage to employ urea, as the least expensive reactant, in excess in order to ensure the optimum utilization of the other reactants.

Alcohol is formed by the reaction of urea with alcoholate as well as by the condensation of the nitrile components into the pyrimidine system. In order to promote the completion of the reaction, the alcohol present in the reaction mixture is advantageously entirely or partly removed during the reaction and no later than prior to the working up of the reaction mixture. By virtue of this important and preferred measure, the reaction is caused to go to completion and the yields are improved, and the alcohol is recovered. The alkali metal salt of the cytosine formed by the reaction can be isolated or converted into the free cytosine by the addition of an acid or an acid anhydride. If sulfuric acid is used for this purpose, the corresponding sulfate is obtained. As an additional method for the preparation of the free cytosine, the saponification of an added ester can be used.

The employment of the solvents which are sparsely miscible with water, moreover, makes it possible to liberate and isolate the cytosine pursuant to a simplified process. In accordance with the present invention, the reaction mixture is worked up by separating the solid substance formed by the reaction, optionally after addition of water. After phase separation with the aid of the above-mentioned neutralization methods, the cytosine is precipitated from the aqueous phase and isolated. After recrystallization from water in the presence of activated charcoal the cytosine can be obtained with high purity and yields of more than 70% of theory.

The separated organic solvent separates from water and can be used for subsequent reactions without separate purification, especially if the preferred alkyl aromatics are used. This recycling increases the product yield to more than 77%.

The mother liquors of the recrystallization can also be used for working up subsequent batches, whereby the yield can be further increased.

Cytosines are useful for the manufacture of pharmaceuticals, agrochemicals as well as photographic chemicals.

The following Examples illustrate the present invention and will enable others skilled in the art to understand it more completely. It should be understood, however, that the invention is not limited solely to the particular Examples given below.

EXAMPLE 1

78.1 g (1.3 mols) of urea and 81.7 g (1.2 mols) of sodium ethylate were suspended in 240 g of xylene, and the suspension was heated to reflux temperature. Over a period of 60 minutes 143.2 g (1 mol) of cyanoacetaldehyde-diethylacetal were added. The resulting mixture was heated at the boiling point for an additional 3 hours, and then the alcohol which had formed during the reaction was distilled off. The residual suspension was admixed with 500 g of water, and the aqueous product phase which formed was separated from the xylene phase. By neutralization of the aqueous phase with 72 g (1.2 mols) of acetic acid, the cytosine was precipitated. Subsequent recrystallization from water in the presence of activated charcoal yielded 82.3 g (74.1% of theory) of pure cytosine.

EXAMPLE 2

78.1 g (1.3 mols) of urea and 81.7 g (1.2 mols) of sodium ethylate were suspended in the xylene phase separated in Example 1, and reacted with 143 g (1 mol) cyanoacetaldehyde-diethylacetal and analogous to Example 1. After working up the reaction mixture as described in Example 1, 85.8 g (77.2% or theory) of pure cytosine were obtained.

EXAMPLE 3

78.1 g (1.3 mols) of urea and 81.7 g (1.2 mols) of sodium ethylate were suspended in 240 g of xylene and the suspension was admixed with 23 g (0.5 mol) of ethanol. The mixture was heated to the reflux temperature, and over the course of 1 hour 143.2 g (1 mol) of cyanoacetaldehyde-diethylacetal were added, and the mixture was heated for 3 additional hours at the boiling point. The alcohol present in the reaction mixture was distilled off, and the residue was admixed with 500 g of water. Cytosine was precipitated from the aqueous phase by the addition of 72 g (1.2 mols) of acetic acid, filtered off and recrystallized from water in the presence of activated charcoal. 81.6 g (73.5% of theory) of cytosine were obtained.

EXAMPLE 4

36 g (0.6 mol) of urea and 37.4 g (0.55 mol) of sodium ethylate were suspended in 150 g of toluene, and the suspension was heated to the boiling point. 48.5 g (0.5 mol) of β-ethoxy-acrylonitrile were added over a period of 30 minutes, and the resulting mixture was heated at the reflux temperature for an additional 4 hours. After removing the ethanol by azeotropic distillation with toluene, the residue was admixed with 250 g of water and worked up as described in Example 1. After recrystallization, 39.6 g (71.4% of theory) of cytosine were isolated.

EXAMPLE 5

39 g (0.65 mol) of urea, 39.1 g (0.575 mol) of sodium ethylate and 71.6 g (0.5 mol) of cyanoacetaldehyde-diethylacetal were combined in 100 g of toluene, and the mixture was heated at its boiling point for 5 hours. Thereafter, the ethanol which had formed was removed by azeotropic distillation with toluene, and the residue was taken up in 250 g of water. After separation of the aqueous phase, cytosine was precipitated by addition of 34.5 g (0.575 mol) of acetic acid, filtered off and purified in analogy to Example 1. 34.1 g (61.3% of theory) of cytosine were obtained.

EXAMPLE 6

78.1 g (1.3 mols) of urea and 81.7 g of sodium ethylate were suspended in 240 g of xylene, and reacted with 132.2 g (1 mol) of cyanoacetaldehyde-diethylacetal in analogy to Example 1. Thereafter, the reaction mixture, without distilling off the alcohol, was admixed with 500 g of water and worked up as described in Example 1. 74.6 g (67.1% of theory) of pure cytosine were obtained.

EXAMPLE 7

39 g (0.65 mol) of urea together with 37.4 g (0.55 mol) of sodium ethylate were suspended in 120 g of dibenzylether, and over a period of 60 mixtures 48.5 g (0.5 mol) of β-ethoxyacrylonitrile were added at 95° C. After heating the reaction mixture for an additional 3 hours at reflux temperature, the ethanol which had formed was distilled off, the residue was admixed with 250 g of water, and the reaction mixture was worked up as described in Example 1. 39.2 g (70.6% of theory) of cytosine were obtained.

EXAMPLE 8

Example 7 was repeated, but 120 g of chlorobenzene were used as the solvent. After working up the reaction mixture as described above, 35.7 g (64.3% of theory) of cytosine were obtained.

EXAMPLE 9

25 g (0.2 mol) of 3-ethoxy-2-ethyl-acrylonitrile were added over a period of 1 hour to a refluxing mixture of 15.6 g (0.26 mol) of urea and 15.7 g (0.23 mol) of sodium ethylate in 50 g of xylene, and the resulting mixture was heated for 3 additional hours at its boiling point. Thereafter, the ethanol in the reaction mixture was distilled off, and the residue was taken up in 120 g of water. The aqueous phase was separated and admixed with 13.8 g (0.23 mol) of acetic acid. The precipitated product was collected by suction filtration and recrystallized from water in the presence of activated charcoal. 18.4 g (66.3% of theory) of pure 5-ethyl-cytosine were obtained.

While the present invention has been illustrated with the aid of certain specific embodiments thereof it will be readily apparent to others skilled in the art that the invention is not limited to these particular embodiments, and that various changes and modifications may be made without departing from the spirit of the invention or the scope of the appended claims.

I claim:

1. In the method of preparing a cytosine of the formula

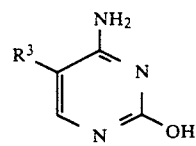

wherein $R^3$ is hydrogen, alkyl of 1 to 6 carbon atoms or aralkyl, which comprises reacting a β-alkoxy-acrylonitrile of the formula

wherein $R^1$ is alkyl of 1 to 6 carbon atoms which may be alkoxy- or halo-substituted, and $R^3$ has the meanings defined above, or a β,β-dialkoxy-propionitrile of the formula

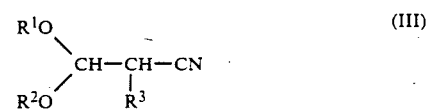

wherein $R^1$ and $R^2$ are alkyl of 1 to 6 carbon atoms which may be alkoxy- or halo-substituted, and $R^3$ has the meanings previously defined, with urea in the presence of an alkali metal alcoholate of the formula MeOR$^4$ wherein $R^4$ is alkyl of 1 to 4 carbon atoms and Me is an alkali metal, and recovering the cytosine by neutralization at temperatures of 0° to 150° C., the improvement which comprises using as a reaction medium a sparsely water-miscible organic solvent or solvent mixture which is inert under the reaction conditions and may contain alcohols as minor components.

2. The method of claim 1, wherein said solvent is a hydrocarbon or an ether.

3. The method of claim 1, wherein said solvent is xylene, cumene, toluene or ethylbenzene.

4. The method of claim 1, wherein the reaction is performed by first combining the urea and the alcoholate at a temperature of 0° to 60° C., and thereafter adding the β-alkoxy-acrylonitrile of the formula II of the β,β-dialkoxy-propionitrile of the formula III continuously or in portions at a temperature of 60° to 130° C.

5. The method of claim 1, wherein the alkali metal alcoholate is the sodium or potassium alcoholate of a lower alkanol.

6. The method of claim 1, wherein the mol ratio of urea to alcoholate is 0.5 to 5:1.

7. The method of claim 1, wherein the mol ratio of urea to alcoholate is 1 to 1.4:1.

8. The method of claim 1, wherein the mol ratio of urea to the nitrile reactant of the formula (II) or (III) is 0,5 to 5:1.

9. The method of claim 1, wherein the mol ratio of urea to nitrile reactant of the formula (II) or (III) is 1 to 2:1.

10. The method of claim 1, wherein the alcohol formed by the reaction is entirely or partly removed from the reaction mixture during the reaction and no later than prior to the working up of the reaction mixture.

11. The method of claim 1, wherein the solid substance formed by the reaction, optionally after dissolution or partial dissolution in water, is separated from the solvent, and the solvent is used again in subsequent reactions for the preparation of cytosine.

* * * * *